US009522098B2

(12) United States Patent
Tuckwell et al.

(10) Patent No.: US 9,522,098 B2
(45) Date of Patent: Dec. 20, 2016

(54) RECONSTITUTION DEVICE

(71) Applicant: Bayer Healthcare LLC, Whippany, NJ (US)

(72) Inventors: Jonathan David Tuckwell, Cambridge (GB); Robert Dyer, Somerville, MA (US); Robert Owen Kivlin, King's Lynn (GB); John Paul Palmer-Felgate, Winchester (GB); Matthew Burgess Avery, Berkeley, CA (US); Kevin George Skinner, Peekskill, NY (US); Chris Kadamus, Chestnut Hill, MA (US); Lee Wood, Bridgend (GB); Peter Schwan, Berkeley, CA (US); Ben Arlett, Cambridge, MA (US)

(73) Assignee: Bayer Healthcare, LLC, Whippany, NJ (US)

( * ) Notice: Subject to any disclaimer, the term of this patent is extended or adjusted under 35 U.S.C. 154(b) by 312 days.

(21) Appl. No.: 14/031,375

(22) Filed: Sep. 19, 2013

(65) Prior Publication Data

US 2014/0166511 A1 Jun. 19, 2014

Related U.S. Application Data

(62) Division of application No. 12/302,197, filed as application No. PCT/US2007/069639 on May 24, 2007, now Pat. No. 8,562,582.

(Continued)

(51) Int. Cl.
*A61B 19/00* (2006.01)
*A61J 1/20* (2006.01)

(52) U.S. Cl.
CPC ............. *A61J 1/2096* (2013.01); *A61J 1/2051* (2015.05); *A61J 1/201* (2015.05); *A61J 1/2055* (2015.05);

(Continued)

(58) Field of Classification Search
CPC ........ A61J 1/201; A61J 1/2096; A61J 1/1418; A61J 1/2055; A61J 1/2075; A61J 1/2086; A61J 1/2082; A61J 29/49826; A61J 1/2051; A61J 1/1412; Y10T 29/49826
See application file for complete search history.

(56) References Cited

U.S. PATENT DOCUMENTS 2,289,677 A 7/1942 Perelson
2,326,490 A 8/1943 Perelson
(Continued)

FOREIGN PATENT DOCUMENTS

EP 161797 11/1985
EP 195018 9/1986
(Continued)

OTHER PUBLICATIONS

International Preliminary Report on Patentability for International Application No. PCT/US2007/069639, completed Jul. 8, 2008.
(Continued)

*Primary Examiner* — Ariana Zimbouski

(57) ABSTRACT

A reconstitution device having an opening surrounded by a neck, and a cap including a first end, a second end, and an inner bore having a central aperture. A stopper is positioned in the opening of the neck and includes a portion capable of being perforated. A plunger is located at the second end of the cap, is configured to slide along the inner bore of the cap, and includes a shaft extending downwardly in a direction towards the stopper and having a pointed end for piercing the stopper. A locking mechanism is located in the cap and includes an aperture. The locking mechanism is configured such that when the plunger is pushed downwardly the shaft is allowed to pass through the aperture, but when the plunger is pulled upwardly the second aperture changes shape such that the shaft cannot freely pass through the aperture.

13 Claims, 10 Drawing Sheets

Related U.S. Application Data

(60) Provisional application No. 60/803,187, filed on May 25, 2006.

(52) U.S. Cl.
CPC ............ *A61J 1/2075* (2015.05); *A61J 1/2082* (2015.05); *A61J 1/2086* (2015.05); *Y10T 29/49826* (2015.01)

(56) References Cited

U.S. PATENT DOCUMENTS 3,478,937 A 11/1969 Solowey
3,739,779 A 6/1973 Pfleger
3,868,965 A 3/1975 Noiles et al.
3,940,003 A 2/1976 Larson
3,941,171 A 3/1976 Ogle
3,977,401 A 8/1976 Pike
3,993,063 A 11/1976 Larrabee
4,084,588 A 4/1978 Koenig
4,128,098 A 12/1978 Bloom et al.
4,152,378 A 5/1979 Vcelka et al.
4,194,640 A 3/1980 Crankshaw et al.
4,211,588 A 7/1980 Raines
4,262,671 A 4/1981 Kersten
4,303,069 A 12/1981 Cohen
4,331,233 A 5/1982 Braymer, Jr.
4,359,166 A 11/1982 Dubach
4,367,738 A 1/1983 Legendre et al.
4,381,776 A 5/1983 Latham, Jr.
4,392,850 A 7/1983 Elias et al.
4,392,851 A 7/1983 Elias
4,410,321 A 10/1983 Pearson et al.
4,479,578 A 10/1984 Brignola et al.
4,493,703 A 1/1985 Butterfield
4,497,415 A 2/1985 Delonghi
4,507,113 A 3/1985 Dunlap
4,516,967 A 5/1985 Kopfer
4,534,482 A 8/1985 Bouche
4,543,101 A 9/1985 Crouch
4,552,277 A 11/1985 Richardson et al.
4,564,054 A 1/1986 Gtavsson
4,573,993 A 3/1986 Hoag et al.
4,576,211 A 3/1986 Valentini et al.
4,582,207 A 4/1986 Howard et al.
4,588,403 A 5/1986 Weiss et al.
4,589,879 A 5/1986 Pearson et al.
4,607,671 A 8/1986 Aalto et al.
4,619,651 A 10/1986 Kopfer et al.
4,624,393 A 11/1986 Lopez
4,657,534 A 4/1987 Beck et al.
4,662,878 A 5/1987 Lindmayer
4,675,020 A 6/1987 McPhee
4,682,689 A 7/1987 Pereira et al.
4,685,917 A 8/1987 Baldini et al.
4,722,733 A 2/1988 Howson
4,735,608 A 4/1988 Sardam
4,759,756 A 7/1988 Forman et al.
4,768,568 A 9/1988 Fournier et al.
4,775,363 A 10/1988 Sandsdalen
4,781,684 A 11/1988 Trenner
4,784,657 A 11/1988 Shimp et al.
4,804,366 A 2/1989 Zdeb et al.
4,826,483 A 5/1989 Molnar, IV
4,834,149 A 5/1989 Fournier et al.
4,834,152 A 5/1989 Howson et al.
4,840,616 A 6/1989 Banks
4,850,978 A 7/1989 Dudar et al.
4,863,427 A 9/1989 Cocchi et al.
4,869,384 A 9/1989 Ogle, II
4,872,494 A 10/1989 Coccia
4,874,366 A 10/1989 Zdeb et al.
4,883,483 A 11/1989 Lindmayer
4,895,570 A 1/1990 Larkin
4,898,209 A 2/1990 Zbed
4,915,692 A 4/1990 Verlier
4,927,423 A 5/1990 Malmborg
4,936,829 A 6/1990 Zdeb et al.
4,941,876 A 7/1990 Meyer et al.
4,950,240 A 8/1990 Greenwood et al.
4,961,728 A 10/1990 Kosinski
4,968,299 A 11/1990 Ahlstrand et al.
5,000,737 A 3/1991 Free et al.
5,024,256 A 6/1991 Vadher
5,037,393 A 8/1991 Ellgass
5,049,129 A 9/1991 Zdeb et al.
5,062,833 A 11/1991 Perler
5,085,332 A 2/1992 Gettig
5,088,996 A 2/1992 Kopfer et al.
5,100,010 A 3/1992 Waters
5,106,372 A 4/1992 Ranford
5,114,411 A 5/1992 Haber et al.
5,116,316 A 5/1992 Sertic et al.
5,122,117 A 6/1992 Haber et al.
5,137,511 A 8/1992 Reynolds
5,167,816 A 12/1992 Kruger et al.
5,171,214 A 12/1992 Kolber et al.
5,176,658 A 1/1993 Ranford et al.
5,188,628 A 2/1993 Rani et al.
5,201,705 A 4/1993 Berglund et al.
5,211,638 A 5/1993 Dudar et al.
5,226,900 A 7/1993 Bancsi et al.
5,232,029 A 8/1993 Knox et al.
5,232,109 A 8/1993 Tirrell et al.
5,247,972 A 9/1993 Tetreault
5,269,429 A 12/1993 Schumacher
5,279,576 A 1/1994 Loo et al.
5,279,582 A 1/1994 Davison et al.
5,279,583 A 1/1994 Shober, Jr. et al.
5,281,198 A 1/1994 Haber et al.
5,303,835 A 4/1994 Haber et al.
5,304,163 A 4/1994 Bonnici et al.
5,314,084 A 5/1994 Folta et al.
5,316,163 A 5/1994 von Schuckmann
5,320,603 A 6/1994 Vetter et al.
5,328,484 A 7/1994 Somers et al.
5,334,162 A 8/1994 Harris
5,336,198 A 8/1994 Silver et al.
5,342,346 A 8/1994 Honda et al.
5,348,174 A 9/1994 Velicka
5,350,372 A 9/1994 Ikeda et al.
5,356,380 A 10/1994 Hoekwater et al.
5,358,501 A 10/1994 Meyer
5,360,410 A 11/1994 Wacks
5,364,369 A 11/1994 Reynolds et al.
5,364,386 A 11/1994 Fukuoka et al.
5,364,387 A 11/1994 Sweeney
5,370,619 A 12/1994 Rossi
5,385,547 A 1/1995 Wong et al.
5,397,303 A 3/1995 Sancoff et al.
5,405,001 A 4/1995 Lillard
5,409,141 A 4/1995 Kikuchi et al.
5,421,469 A 6/1995 Lee
5,423,753 A 6/1995 Fowles et al.
5,429,256 A 7/1995 Kestenbaum
5,429,614 A 7/1995 Fowles et al.
5,445,631 A 8/1995 Uchida
5,454,409 A 10/1995 Mcaffer et al.
5,454,786 A 10/1995 Harris
5,456,678 A 10/1995 Nicoletti
5,464,123 A 11/1995 Scarrow
5,472,434 A 12/1995 Lechleiter
5,474,209 A 12/1995 Vallet Mas et al.
5,478,337 A 12/1995 Okamoto et al.
5,487,737 A 1/1996 Meyer
5,489,266 A 2/1996 Grimard
5,522,804 A 6/1996 Lynn
5,526,853 A 6/1996 McPhee et al.
5,533,994 A 7/1996 Meyer
5,534,228 A 7/1996 Wesseler
5,554,125 A 9/1996 Reynolds et al.
5,562,616 A 10/1996 Haber et al.
5,566,729 A 10/1996 Grabenkort et al.
5,569,193 A 10/1996 Hofstetter et al.

(56) References Cited

U.S. PATENT DOCUMENTS 5,613,291 A 3/1997 Solomon et al.
5,636,660 A * 6/1997 Pfleiderer ............ A61J 1/2089 137/550
5,637,087 A 6/1997 O'Neil et al.
5,641,010 A 6/1997 Maier
5,685,845 A 11/1997 Grimard
5,685,846 A 11/1997 Michaels, Jr.
5,702,019 A 12/1997 Grimard
5,709,666 A 1/1998 Reynolds
5,709,668 A 1/1998 Wacks
5,711,443 A * 1/1998 Bennett ............. B65D 41/3428 215/251
5,713,875 A 2/1998 Tanner, II
5,743,312 A 4/1998 Pfeifer et al.
5,752,940 A 5/1998 Grimard
5,766,147 A 6/1998 Sancoff et al.
5,769,825 A 6/1998 Lynn
5,772,652 A 6/1998 Zielinski
5,776,124 A 7/1998 Wald
5,779,668 A 7/1998 Grabenkort
5,779,683 A 7/1998 Meyer
5,785,682 A 7/1998 Grabenkort
5,785,701 A 7/1998 Sams et al.
5,791,466 A 8/1998 Tsals
5,797,897 A 8/1998 Jepson et al.
5,817,082 A 10/1998 Niedospial, Jr. et al.
5,826,713 A 10/1998 Sunago et al.
5,827,262 A 10/1998 Neftel et al.
5,833,213 A 11/1998 Ryan
5,855,575 A 1/1999 Solomon et al.
5,865,798 A 2/1999 Grimard et al.
5,871,110 A 2/1999 Grimard et al.
5,871,500 A 2/1999 Jepson et al.
5,873,872 A 2/1999 Thibault et al.
5,876,372 A 3/1999 Grabenkort et al.
5,879,345 A 3/1999 Aneas
5,890,610 A 4/1999 Jansen et al.
5,891,129 A 4/1999 Daubert et al.
5,893,397 A 4/1999 Peterson et al.
5,895,383 A 4/1999 Niedospial, Jr.
5,899,881 A 5/1999 Grimard et al.
5,899,888 A 5/1999 Jepson et al.
5,902,298 A 5/1999 Niedospial, Jr. et al.
5,924,584 A 7/1999 Hellstrom et al.
5,925,029 A 7/1999 Jansen et al.
5,927,531 A 7/1999 Kuzma et al.
5,954,104 A 9/1999 Daubert et al.
5,957,314 A 9/1999 Nishida et al.
5,957,898 A 9/1999 Jepson et al.
5,964,739 A 10/1999 Champ
5,971,953 A 10/1999 Bachynsky
5,989,237 A 11/1999 Fowles et al.
6,003,566 A 12/1999 Thibault et al.
6,003,702 A 12/1999 Grimard et al.
6,019,750 A 2/2000 Fowles et al.
6,022,339 A 2/2000 Fowles et al.
6,063,068 A 5/2000 Fowles et al.
6,070,623 A * 6/2000 Aneas .................. A61J 1/2096 141/27
6,071,270 A 6/2000 Fowles et al.
6,090,091 A 7/2000 Fowles et al.
6,090,092 A 7/2000 Fowles et al.
6,090,093 A 7/2000 Thibault et al.
6,102,893 A 8/2000 Aneas
6,113,583 A 9/2000 Fowles et al.
6,123,685 A 9/2000 Reynolds
6,139,534 A 10/2000 Niedospial, Jr. et al.
6,146,362 A 11/2000 Turnbull et al.
6,149,623 A 11/2000 Reynolds
6,159,192 A 12/2000 Fowles et al.
6,168,037 B1 1/2001 Grimard
6,171,293 B1 1/2001 Rowley
6,183,464 B1 2/2001 Sharp
6,189,580 B1 2/2001 Thibault et al.
6,189,688 B1 2/2001 Aneas
6,209,738 B1 4/2001 Jansen et al.
6,213,994 B1 4/2001 Jansen et al.
6,237,649 B1 5/2001 Moisio et al.
6,238,372 B1 5/2001 Zinger et al.
6,257,454 B1 7/2001 Ritsche
6,258,078 B1 7/2001 Thilly
6,261,266 B1 7/2001 Jepson et al.
6,261,282 B1 7/2001 Jepson et al.
6,267,154 B1 7/2001 Felicelli et al.
6,269,976 B1 8/2001 Dejonge
6,280,430 B1 8/2001 Neftel et al.
6,299,608 B1 10/2001 Solomon et al.
6,344,033 B1 2/2002 Jepson et al.
6,349,850 B1 2/2002 Cheikh
6,358,236 B1 3/2002 Defoggi et al.
6,378,576 B2 4/2002 Thibault et al.
6,378,714 B1 4/2002 Jansen et al.
6,379,340 B1 4/2002 Zinger et al.
6,382,442 B1 5/2002 Thibault et al.
6,398,031 B1 6/2002 Frezza
6,406,455 B1 6/2002 Willis et al.
6,426,049 B1 7/2002 Rosen et al.
6,440,101 B1 8/2002 Grabenkort et al.
6,453,956 B2 9/2002 Safabash
6,474,375 B2 11/2002 Spero et al.
6,478,788 B1 11/2002 Aneas
6,524,295 B2 2/2003 Daubert et al.
6,527,738 B1 3/2003 Jones et al.
6,537,263 B1 3/2003 Aneas
6,551,299 B2 4/2003 Miyoshi et al.
6,558,365 B2 5/2003 Zinger et al.
6,562,002 B1 5/2003 Taylor
6,569,125 B2 5/2003 Jepson et al.
6,571,837 B2 6/2003 Jansen et al.
6,582,415 B1 6/2003 Fowles et al.
6,585,695 B1 7/2003 Adair et al.
6,591,876 B2 7/2003 Safabash
6,595,964 B2 7/2003 Finley et al.
6,601,721 B2 8/2003 Jansen et al.
6,610,040 B1 8/2003 Fowles et al.
6,610,041 B2 8/2003 Daubert et al.
6,626,309 B1 9/2003 Jansen et al.
6,635,043 B2 10/2003 Daubert et al.
6,638,244 B1 10/2003 Reynolds
6,645,171 B1 11/2003 Robinson et al.
6,652,509 B1 11/2003 Helgren et al.
6,656,433 B2 12/2003 Sasso
6,659,296 B2 12/2003 Browne
6,666,852 B2 12/2003 Niedospial, Jr.
6,669,681 B2 12/2003 Jepson et al.
6,673,035 B1 1/2004 Rice et al.
6,673,038 B2 1/2004 Weston
6,681,810 B2 1/2004 Weston
6,681,946 B1 1/2004 Jansen et al.
6,682,509 B2 1/2004 Lopez
6,684,918 B1 2/2004 Thilly et al.
6,685,692 B2 2/2004 Fathallah
6,699,229 B2 3/2004 Zinger et al.
6,706,031 B2 3/2004 Manera
6,709,424 B1 3/2004 Knierbein
6,715,520 B2 4/2004 Andréasson et al.
6,723,068 B2 4/2004 Lavi et al.
6,729,370 B2 5/2004 Norton et al.
6,758,833 B2 7/2004 Lopez
6,779,566 B2 8/2004 Engel
6,790,199 B1 9/2004 Gianakos
6,793,646 B1 9/2004 Giambattista et al.
6,837,872 B2 1/2005 Crawford
6,852,103 B2 2/2005 Fuller et al.
6,874,522 B2 4/2005 Anderson et al.
6,875,203 B1 4/2005 Fowles et al.
6,875,205 B2 4/2005 Leinsing
6,890,328 B2 5/2005 Fowles et al.
6,893,420 B2 5/2005 Arnisolle
6,902,543 B1 6/2005 Cherif-Cheikh et al.
6,932,791 B2 8/2005 Taylor
6,945,417 B2 9/2005 Jansen et al.
6,948,522 B2 9/2005 Newbrough et al.
6,957,745 B2 10/2005 Thibault et al.

(56) References Cited

U.S. PATENT DOCUMENTS

| | | | |
|---|---|---|---|
| 6,997,917 | B2 | 2/2006 | Niedospial, Jr. et al. |
| 7,008,406 | B2 | 3/2006 | Mayer |
| 7,025,389 | B2 | 4/2006 | Cuschieri et al. |
| 7,041,087 | B2 | 5/2006 | Henderson et al. |
| 7,074,216 | B2 | 7/2006 | Fowles et al. |
| 7,077,176 | B2 | 7/2006 | Py |
| 7,077,835 | B2 | 7/2006 | Robinson et al. |
| 7,083,596 | B2 | 8/2006 | Saied |
| 7,086,431 | B2 | 8/2006 | D'Antonio et al. |
| 7,140,401 | B2 | 11/2006 | Wilcox et al. |
| 7,186,241 | B2 | 3/2007 | Py |
| 7,188,750 | B2 | 3/2007 | Vogel et al. |
| 7,195,616 | B2 | 3/2007 | Diller et al. |
| 7,195,623 | B2 | 3/2007 | Burroughs et al. |
| 7,198,611 | B2 | 4/2007 | Connell et al. |
| 7,232,419 | B2 | 6/2007 | Castellanos |
| 7,258,119 | B2 | 8/2007 | Mazzoni |
| 7,261,707 | B2 | 8/2007 | Frezza et al. |
| 7,294,122 | B2 | 11/2007 | Kubo et al. |
| 7,297,140 | B2 | 11/2007 | Orlu et al. |
| 7,326,194 | B2 | 2/2008 | Zinger et al. |
| 7,350,535 | B2 | 4/2008 | Liepold et al. |
| 7,358,505 | B2 | 4/2008 | Woodworth et al. |
| 7,374,558 | B2 | 5/2008 | Kirchhofer |
| 7,387,623 | B2 | 6/2008 | Macleod |
| 7,407,495 | B2 | 8/2008 | Barere et al. |
| 7,425,209 | B2 | 9/2008 | Fowles et al. |
| 7,452,348 | B2 | 11/2008 | Hasegawa |
| 7,470,257 | B2 | 12/2008 | Norton et al. |
| 7,470,258 | B2 | 12/2008 | Barker et al. |
| 7,491,197 | B2 | 2/2009 | Jansen et al. |
| 7,537,582 | B2 | 5/2009 | Suresh et al. |
| 7,632,261 | B2 | 12/2009 | Zinger et al. |
| 7,879,018 | B2 | 2/2011 | Zinger et al. |
| 8,172,824 | B2 | 5/2012 | Pfeifer et al. |
| 8,225,949 | B2 | 7/2012 | Aneas |
| 8,628,508 | B2 | 1/2014 | Weitzel et al. |
| 2001/0000347 | A1 | 4/2001 | Hellstrom et al. |
| 2001/0000793 | A1 | 5/2001 | Daubert et al. |
| 2001/0000794 | A1 | 5/2001 | Daubert et al. |
| 2001/0003996 | A1 | 6/2001 | Jansen et al. |
| 2001/0025672 | A1 | 10/2001 | Thibault et al. |
| 2002/0087144 | A1 | 7/2002 | Zinger et al. |
| 2002/0121496 | A1 | 9/2002 | Thiebault et al. |
| 2002/0128629 | A1 | 9/2002 | Antoine |
| 2002/0193777 | A1 | 12/2002 | Aneas |
| 2003/0040697 | A1 | 2/2003 | Pass et al. |
| 2003/0069538 | A1 | 4/2003 | Pfeifer et al. |
| 2003/0075168 | A2 | 4/2003 | Alchas |
| 2003/0107628 | A1 | 6/2003 | Fowles et al. |
| 2003/0192791 | A1 | 10/2003 | Eek et al. |
| 2003/0199846 | A1 | 10/2003 | Fowles et al. |
| 2004/0044327 | A1 | 3/2004 | Hasegawa |
| 2004/0073189 | A1 | 4/2004 | Wyatt et al. |
| 2004/0112457 | A1 | 6/2004 | Norton et al. |
| 2004/0124389 | A1 | 7/2004 | Phillips |
| 2004/0127858 | A1 | 7/2004 | Bendek et al. |
| 2004/0199139 | A1 | 10/2004 | Fowles et al. |
| 2004/0210207 | A1 | 10/2004 | Amisar et al. |
| 2004/0236305 | A1 | 11/2004 | Jansen et al. |
| 2004/0238776 | A1 | 12/2004 | Peters et al. |
| 2005/0070853 | A1 | 3/2005 | Gatton et al. |
| 2005/0137523 | A1 | 6/2005 | Wyatt et al. |
| 2005/0203481 | A1 | 9/2005 | Orlu et al. |
| 2006/0025747 | A1 | 2/2006 | Sullivan et al. |
| 2006/0069350 | A1 | 3/2006 | Buenger et al. |
| 2006/0079834 | A1 | 4/2006 | Tennican et al. |
| 2006/0089594 | A1 | 4/2006 | Landau |
| 2006/0089601 | A1 | 4/2006 | Dionigi |
| 2006/0116644 | A1 | 6/2006 | Norton |
| 2006/0155257 | A1 | 7/2006 | Reynolds |
| 2006/0167411 | A1 | 7/2006 | Weston et al. |
| 2006/0203608 | A1 | 9/2006 | Barker et al. |
| 2006/0229572 | A1 | 10/2006 | Lopez |
| 2006/0287638 | A1 | 12/2006 | Aneas |
| 2007/0060904 | A1 | 3/2007 | Vedrine et al. |
| 2007/0068594 | A1* | 3/2007 | Fischer ................ A61J 1/2096 141/27 |
| 2007/0088313 | A1 | 4/2007 | Zinger et al. |
| 2007/0106244 | A1 | 5/2007 | Mosler et al. |
| 2007/0112324 | A1 | 5/2007 | Hamedi-Sangsari |
| 2007/0167904 | A1 | 7/2007 | Zinger et al. |
| 2007/0173783 | A1 | 7/2007 | Haindl |
| 2007/0270778 | A9 | 11/2007 | Zinger et al. |
| 2007/0293826 | A1 | 12/2007 | Wall et al. |
| 2007/0299395 | A1 | 12/2007 | Pelkey et al. |
| 2008/0009789 | A1 | 1/2008 | Zinger et al. |
| 2008/0045919 | A1 | 2/2008 | Jakob et al. |
| 2008/0154176 | A1 | 6/2008 | Van Ingelgem et al. |
| 2008/0154196 | A1 | 6/2008 | Moh |
| 2008/0172024 | A1 | 7/2008 | Yow |
| 2008/0188799 | A1 | 8/2008 | Mueller-Beckhaus et al. |
| 2008/0214998 | A1 | 9/2008 | Kurek et al. |
| 2008/0249479 | A1 | 10/2008 | Zinger et al. |
| 2008/0287914 | A1 | 11/2008 | Wyatt et al. |
| 2008/0300570 | A1 | 12/2008 | Fowles et al. |
| 2008/0319346 | A1 | 12/2008 | Crawford et al. |
| 2009/0043282 | A1 | 2/2009 | Hughes et al. |

FOREIGN PATENT DOCUMENTS

| | | | |
|---|---|---|---|
| EP | 796604 | | 9/1997 |
| EP | 829250 | | 3/1998 |
| EP | 959867 | | 1/1999 |
| EP | 898951 | | 3/1999 |
| EP | 0904764 | | 3/1999 |
| EP | 1205173 | | 5/2002 |
| EP | 1351733 | | 10/2003 |
| EP | 1434549 | | 7/2004 |
| EP | 1454609 | | 8/2004 |
| EP | 1454650 | | 8/2004 |
| EP | 1487533 | | 12/2004 |
| EP | 1799285 | | 6/2007 |
| EP | 1820485 | | 8/2007 |
| FR | 2753624 | | 3/1998 |
| FR | 2780878 | | 1/2000 |
| GB | 1419061 | | 12/1975 |
| JP | 50-23194 | | 3/1975 |
| JP | H06296662 | A | 10/1994 |
| JP | 11-503627 | | 3/1999 |
| JP | 2001505083 | | 4/2001 |
| JP | 2004-511306 | | 4/2004 |
| JP | 2005-102782 | | 4/2005 |
| WO | 97/42305 | | 11/1997 |
| WO | 98/32411 | | 7/1998 |
| WO | 9832411 | A1 | 7/1998 |
| WO | 99/27886 | | 10/1999 |
| WO | 2007068823 | A1 | 6/2007 |
| WO | 2007068825 | A1 | 6/2007 |
| WO | 2007/148708 | | 12/2007 |

OTHER PUBLICATIONS

Written Opinion of the International Searching Authority for International Application No. PCT/US2007/069639, mailed Mar. 3, 2008.

Communication pursuant to Article 94(3) EPC for European Patent Application No. 07762 316.3-1257, Aug. 16, 2010.

Invitation to Pay Additional Fees for International Patent Application No. PCT/US2007/069639, mailed Jan. 9, 2008.

International Search Report for International Patent Application No. PCT/US2007/069639, mailed Mar. 3, 2008.

* cited by examiner

RECONSTITUTION DEVICE

CROSS-REFERENCE TO RELATED APPLICATIONS

This application is a divisional application of U.S. application Ser. No. 12/302,197, filed Feb. 11, 2010, the entire disclosure of which is incorporated herein.

FIELD OF THE INVENTION

The present application relates generally to reconstitution devices. More particularly, the application relates to an improved reconstitution device for connecting a closed receptacle and a container, such as a syringe.

DESCRIPTION OF RELATED ART

In the domain of drug-packaging, it is known to store a component of a medicinal preparation, such as for example its active ingredient, in a recipient closed by a stopper of relatively non-rigid material, for example of elastomer. A liquid may be introduced into this recipient after perforation of the stopper in order to dissolve the component contained in the recipient or place it in suspension, with a view to obtaining a medicinal preparation in liquid form ready to be administered to the patient.

Traditional devices include a base adapted to cover the neck of the recipient and extending in a flange forming an inner bore while a plunger is adapted to slide in the bore, between a position disengaged with respect to the stopper and an engaged position in which a hollow needle borne by the plunger traverses this stopper. The displacement of the plunger from its disengaged position towards its engaged position is effected manually by an operator.

However, traditional devices do not include an actuating mechanism to prevent unwanted use of the device and to facilitate user interaction. Since the reconstitution device is not meant to be reused, unwanted actuation of the device could be wasteful and incur unnecessary costs. Furthermore, traditional devices do not prevent the device from being reused.

Accordingly, it is desirable to develop a reconstitution device that facilitates user interaction by increasing the likelihood that the user follows the proper steps in the reconstitution process, as well as sufficiently preventing the device from being inadvertently actuated or reused.

SUMMARY

The present invention is directed to a reconstitution device. In accordance with an exemplary embodiment of the invention, the reconstitution device generally comprises a receptacle having an opening surrounded by a neck, and a cap including a first end, a second end, and an inner bore having a central aperture, with the first end being secured to the receptacle. A stopper is positioned in the opening of the neck, with the stopper including a portion capable of being perforated. A plunger is located at the second end of the cap. The plunger is configured to slide along the inner bore of the cap and includes a shaft extending downwardly in a direction towards the stopper and having a pointed end for piercing the portion of the stopper upon downward movement of the plunger. A locking mechanism is located in the cap and includes an aperture. The locking mechanism is configured such that when the plunger is pushed downwardly the shaft is allowed to pass through the aperture, but when the plunger is pulled upwardly the second aperture changes shape such that the shaft cannot freely pass through the aperture.

The present invention helps to solve the shortcomings of the prior art by facilitating user interaction by increasing the likelihood that the user follows the proper steps in the reconstitution process. The device further provides an improved means of tamper-proofing than currently available reconstitution devices. These as well as other aspects and advantages will become apparent to those of ordinary skill in the art by reading the following detailed description, with reference where appropriate to the accompanying drawings. Further, it should be understood that the embodiments described in this summary and elsewhere are intended to illustrate the invention by way of example only.

BRIEF DESCRIPTION OF THE DRAWINGS

Exemplary embodiments of the invention are described herein with reference to the drawings, in which.

DETAILED DESCRIPTION

Figure 1:
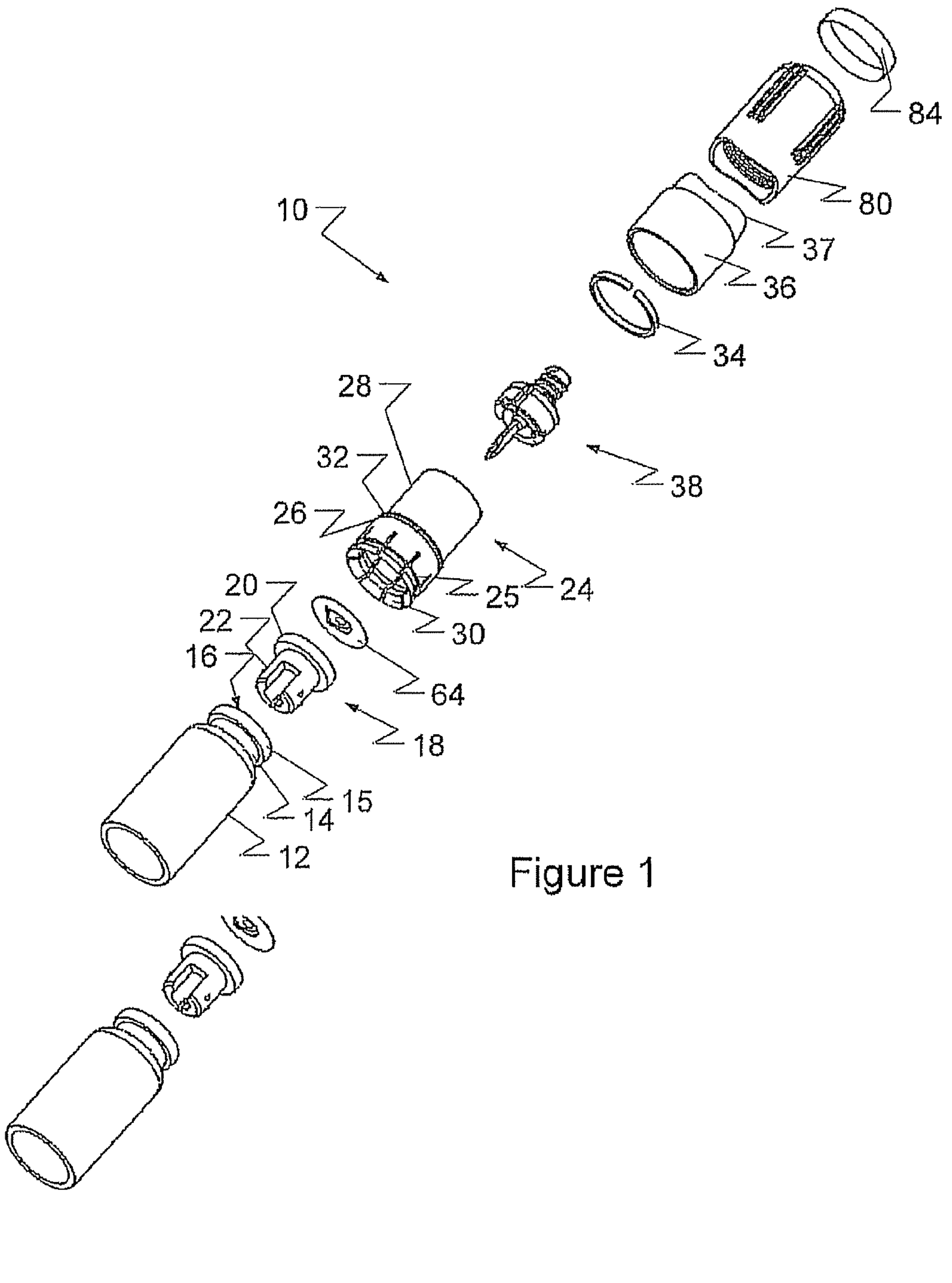
FIG. 1 is an expanded view of a reconstitution device of the present invention.

FIG. 1 depicts a reconstitution device 10. The device 10 may include a receptacle 12 for storing a first component of a pharmaceutical preparation (not shown), such as its active ingredient, for example. The receptacle 12 may include an opening 16 surrounded or partially surrounded by a neck 14. The neck 14 may also include a lip 15. The opening 16 in the neck 14 allows for a second component (not shown), such as a liquid, to be introduced into the receptacle 12 and mix with the first component. A stopper 18 may be positioned in the opening 16 of the neck 14 to block access to the receptacle 12. The stopper 18 may be made of a relatively non-rigid material, such as elastomer. The stopper 18 may include a top portion 20 located against the lip 15, and a bottom portion 22 located within the opening of the neck 14. The top portion 20 may be capable of being perforated, thereby allowing access to the receptacle 12.

The device 10 may further include a cap 24 secured to the neck 14 of the receptacle 12. The cap 24 may have a first end 26, which is secured to the neck 14 of the receptacle 12, and a second end 28 located opposite the first end 26. The first end 26 of the cap 24 may surround at least a portion of the stopper 18. The first end 26 of the cap 24 may include one or more flexible legs 30 so the cap 24 can expand to fit over the lip 15 of the neck 14 during the manufacturing process, and then contract to securely mate with the neck 14. The cap 24 may further include a step portion 32 located between the first end 26 and the second end 28, thereby separating the first end 26 from the second end 28. The first end 26 of the cap 24 may have a larger diameter than the second end 28 of the cap 24.

The first end 26 of the cap 24 may be secured to the receptacle 12 by a C-clip 34, which may be positioned in an indentation 25 in the first end 26 of the cap 24. Therefore, the C-clip 34 is not located directly on the neck 14 of the receptacle 12 and no scratching occurs. The C-clip 34 may be made of a material not subject to heat degradation, such as metal for example, so that the device 10 may be resistant to heat tampering.

The first end 26 of the cap may be surrounded by a sleeve 36 for protection. The sleeve 36 is prevented from sliding off the cap 24 by the step portion 32. The sleeve 36 may include a wave-shaped part 37 to facilitate opening by a user (not shown), as can be seen in detail in FIG. 6. The sleeve 36 may further include a textured surface to facilitate gripping of the device 10 by a user.

Assembly of the first end 26 of the cap 24 to the receptacle 12 may be carried out using various methods. For example, an assembly method may include initially inserting the C-clip 34 into the indentation 25, and then sliding the cap 24 over the stopper 18 and the lip 15. As another example, an assembly method may include initially placing the C-clip 34 onto the second end 28 of the cap 24, then sliding the sleeve 36 over the second end 28 in such a way that the sleeve 36 contacts the C-clip 34 and pushes the C-clip 34 into the indentation 25, and then sliding the cap 24 over the stopper 18 and the lip 15. In accordance with these exemplary methods, as the cap 24 is slid over the stopper 18 and the lip 15, the opening in the C-clip 34 allows the flexible legs 30 to expand as the flexible legs 30 pass over the lip 15, and the flexible legs 30 may contract after passing over the lip 15 to secure the cap to the receptacle 12.

Figure 2:
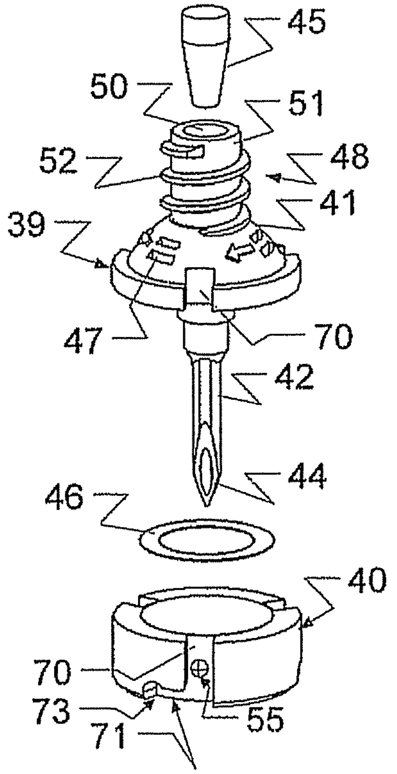
FIG. 2 is an expanded view of the plunger shown in FIG. 1.

FIG. 2 depicts details of a plunger 38 located at the second end 28 of the cap 24. The cap 24 may also include a ridge 35, shown in FIG. 3, which may be used to secure the plunger 38 within the cap 24. The plunger 38 may comprise a first portion 39. The first portion 39 of the plunger 38 may include a top surface 41. The top surface 41 may be arranged in various configurations. For example, the top surface 41 may be dome-shaped (i.e., a domed top surface). As another example, the top surface 41 may be angled (i.e., an angled top surface). Other exemplary configurations of the top surface 41 are also possible.

The first portion 39 of the plunger 38 may further include a shaft 42 extending downwardly in a direction towards the stopper 18. The shaft 42 may include a pointed end 44 for piercing the top portion 20 of the stopper 18, thereby allowing the shaft 42 access to the receptacle 12. The pointed end 44 may be angled to cooperate with a locking mechanism 64, which is described in detail below. In one embodiment, the shaft 42 is elliptical-shaped (e.g., oval shaped). The shaft 42 being elliptical-shaped requires less applied force when the shaft 42 pierces the stopper 18. In alternative embodiments, the shaft 42 may have a cylindrical shape or a rectangular shape.

The plunger 38 may comprise a second portion 40 which is located below the first portion 39. The second portion 40 of the plunger 38 preferably has the same shape as the first portion 39, (e.g., an elliptical shape, a cylindrical shape, or a rectangular shape).

In one exemplary embodiment, the first portion 39 of the plunger 38 is permanently attached to the second portion 40 of the plunger 38 so as to prevent leaks (e.g., a fluid leak) between where the first portion 39 mates to the second portion 40. Various methods may be used to permanently attach the first portion 39 of the plunger 38 to the second portion 40 of the plunger 38. For example, the first portion 39 of the plunger 38 may be permanently attached to the second portion 40 of the plunger 38 by ultrasonic welding. As another example, the first portion 39 of the plunger 38 may be permanently attached to the second portion 40 of the plunger 38 by use of an adhesive (e.g., a glue). Other exemplary methods for permanently attaching the first portion 39 of the plunger 38 to the second portion 40 of the plunger 38 are also possible.

The plunger 38 may further include one or more filtering mechanisms. For example, a fluid filter 45 may be located in the first portion 39 of the plunger so as to filter any liquid that is introduced into the plunger 38. Furthermore, an air filter 46 may be located in a cavity 49 (shown in FIG. 3) between the first portion 39 of the plunger 38 and the second portion 40 of the plunger 38 so as to filter any air that is introduced into the receptacle 12. The air filter 46 may be made from any of a variety of materials, but is preferably made of polyethersulphone (PES). Both filters may be located in line with the shaft 42 of the plunger 38.

Figure 8A:
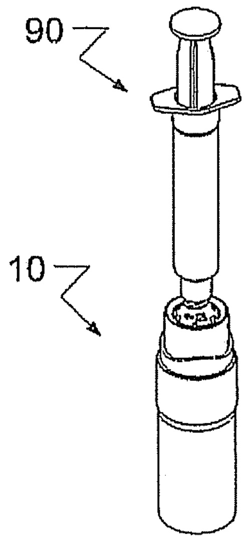
FIGS. 8A and 8B are perspective views of a second receptacle in use with the reconstitution device of FIG. 1.
Figure 8B:
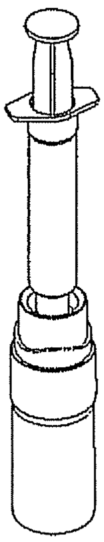

The first portion 39 of the plunger 38 may include a male element 48 extending from the top surface 41 in an upward direction opposite the shaft 42. The male element 48 may be configured to receive a second receptacle 90, such as a syringe, for example, as shown in FIGS. 8A and 88. The male element 48 may include an inner bore 50 and an outer surface 51. The outer surface 51 may include a thread 52 for mating with the second receptacle 90.

An advantage of the dome or angled shape of the top surface 41 is that the male element 48 visibly extends above the top surface 41. When the male element 48 receives the second receptacle 90 (e.g., by fastening a threaded syringe to the thread 52 of the male element 48), a user can clearly see when the second receptacle 90 is not in contact with the top surface 41. In this way, a user fastening the second receptacle 90 can continue to turn the second receptacle 90 and clearly tell when the second receptacle 90 makes contact with the top surface 41. Thus, the user knows when second receptacle 90 is fully secured to the male element 48.

Figure 3:
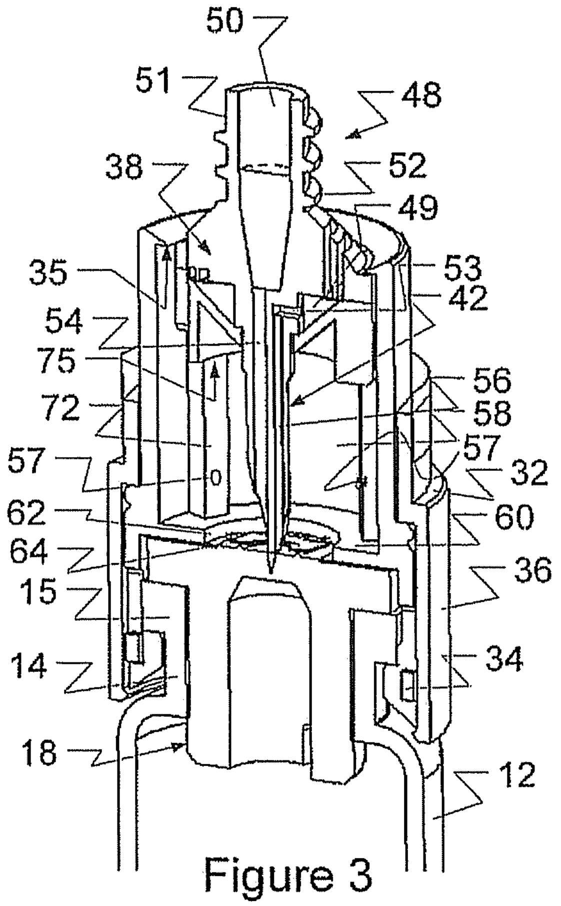
FIG. 3 is a cross-sectional view of the reconstitution device of FIG. 1.

Referring to FIG. 3, the shaft 42 of the plunger 38 may include a first longitudinal channel 54. The first longitudinal channel 54 establishes communication between the receptacle 12 and the inner bore 50 of the male element 48. The first channel 54 may allow fluid to pass through the shaft 42 of the plunger 38 and into the receptacle 12.

The shaft 42 of the plunger 38 may include a second longitudinal channel 56. The end of the second channel 56 located opposite the pointed end 44 of the shaft 42 may interface to an air channel return 53. The air channel return 53 interfaces to a cavity 49. The cavity 49 is formed by joining the first portion 39 of the plunger 38 to the second portion 40 of the plunger 38. The second channel 56 functions as an air path to allow air to travel out of the receptacle 12 through the shaft 42 of the plunger 38, into the air channel return 53, through the filter 46, and then through the vent 47 located on the top surface 41 of the plunger 38. The air exiting the vent 47 is vented to the atmosphere surrounding the device 10.

Figure 4:
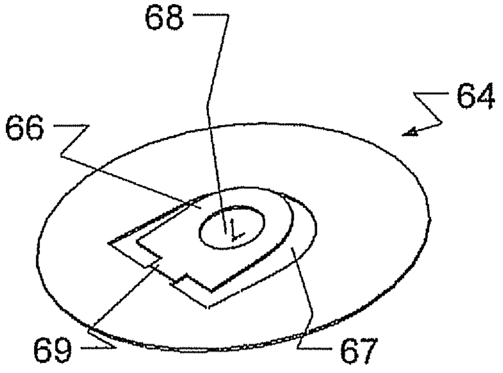
FIGS. 4, 4A, and 4B are various views of the locking mechanism of the device of FIG. 1.
Figure 4A:
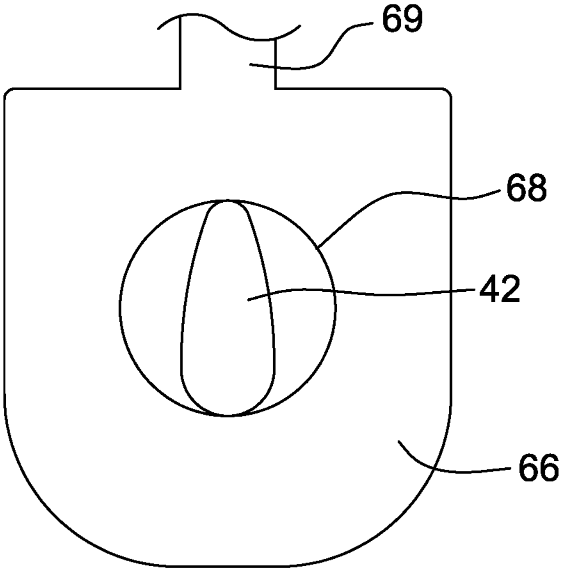
Figure 4B:
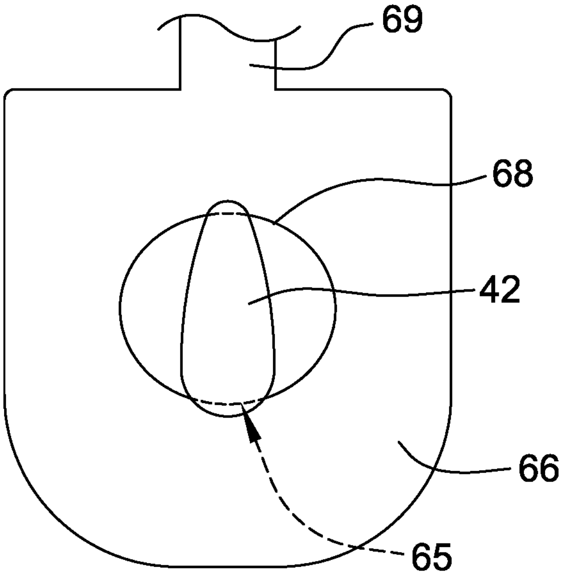
Figure 9:
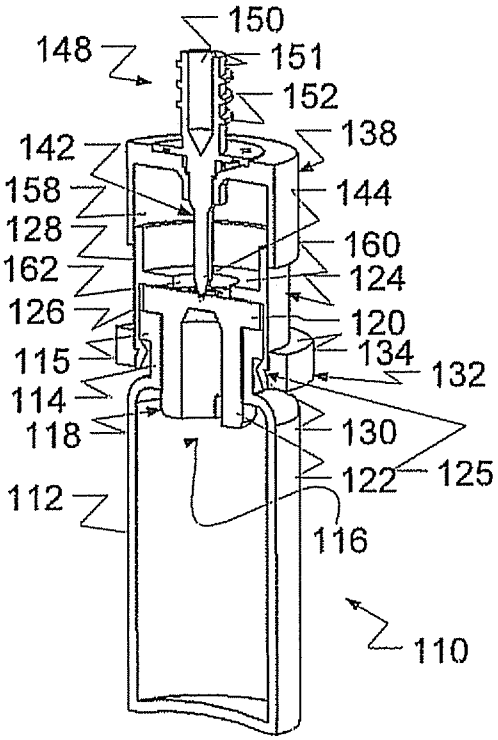
FIG. 9 is a cross-sectional view of a second embodiment of a reconstitution device of the present invention.

The cap 24 may further include an inner bore 58 having an annular plate 60 with an aperture 62. The aperture 62 is coaxially aligned with the shaft 42 of the plunger 38. The plunger 38 may be configured to slide along the inner bore 58 of the cap 24, or alternatively, the plunger 38 may be configured to slide along an outer surface of the cap, as shown in FIG. 9, which will be described below. When the plunger 38 is pushed downward toward the receptacle 12, the shaft 42 moves downwardly through the aperture 62 to pierce the top portion 20 of the stopper 18. With particular reference to FIGS. 4-4B, the device 10 may include a locking mechanism 64 for preventing upward movement of the plunger 38 after downward movement of the plunger 38 has occurred. In this manner, the device 10 may be prevented from multiple uses by restraining the plunger 38 in an engaged position, that is, when the shaft 42 pierces the stopper 18.

The locking mechanism 64 may use St. Venant's principle, which states deformations due to stress concentrations are not observed at a distance of three major diameters from the stress concentration. In accordance with this principle, if the locking mechanism 64 is made of a thin material that deforms an area of the shaft 42 greater than the thickness of the thin material as the shaft 42 is moved in a downward direction, then the locking mechanism 64 will prevent the shaft 42 from moving in an upward direction because the locking mechanism will fall in the deformed area of the shaft 42.

As shown in FIG. 4, the locking mechanism 64 may include a thin, cylindrically shaped material. Alternatively, the locking mechanism 64 could be another shape such as elliptical or rectangular. The locking mechanism 64 may be made of any flexible material, such as metal or plastic, for example.

The locking mechanism 64 may be located at various locations within the device 10. For example, as shown in FIG. 3, the locking mechanism 64 may be located below the annular plate 60. As another example, the locking mechanism 64 may be located above the annular plate 60. As yet another example, the locking mechanism 64 could be incorporated into the cap 24 (e.g., the locking mechanism could be made of the same material as the cap 24 and molded to the cap 24).

The locking mechanism 64 may include a tongue 66 extending therefrom, and being located within a first aperture 67 of the locking mechanism 64. The tongue 66 may be connected to the first aperture 67 at tab 69, and therefore the tongue 66 is capable of flexing in the vertical direction. The tongue 66 may include a second aperture 68 that is coaxially aligned with the shaft 42. The diameter of the second aperture 68 may be slightly larger than the diameter of the shaft 42. The tongue 66 may be bent upward, as shown in FIG. 4.

In operation, the locking mechanism 64 functions as a unidirectional cam. When the plunger 38 is pushed downwardly (as shown in FIG. 4A), the shaft 42 presses the tongue 66 downwardly, thereby opening the second aperture 68 enough to allow the shaft 42 to pass through the second aperture 68 and pierce the stopper 18. The locking mechanism 64 is triggered when a user attempts to pull the plunger 38 upwardly after the plunger 38 has been pushed downwardly.

When the plunger 38 is pulled upwardly (as shown in FIG. 4B), the shaft 42 pulls upwardly on the tongue 66 which causes the tongue 66 to flex vertically in an upward direction. The flexing causes the second aperture 68 to change shape from a first shape (e.g., a cylindrical shape (FIG. 4A) when the second aperture 68 is substantially perpendicular to the shaft 42) to a second shape (e.g., an elliptical shape (FIG. 4B) when the second aperture 68 is in a position not perpendicular to the shaft 42). In this way, the shape of the second aperture 68 may be different from the shape of the shaft 42. Since the shaft 42 cannot freely pass through the second aperture 68 due in part to their different shapes, the tongue 66 then cuts into the shaft 42, creating a stress concentration, or notch 65, in the shaft 42. The second aperture 68 in the tongue 66 fits into the notch 65 and prevents the plunger 38 from upward movement. Therefore, the plunger 38 may not be removed from the stopper 18, or moved in an upward direction, without damaging the device 10.

The locking mechanism 64 ensures a smooth downward motion of the plunger 38 with low actuation force and prevents reuse of the device 10 by retaining the plunger 38 in a downward position due to a high retaining force (relative to the actuation force). The locking mechanism 64 may prevent return motion at any point during the downward movement of the shaft 42. Thus, the locking mechanism 64 improves upon retaining clips used in other reconstitution devices to secure a plunger only after the plunger has reached the most downward point of the plunger's downward travel.

The device 10 may include an actuating mechanism. The actuating mechanism may include at least one indentation 70 located on an outer circumference of the plunger 38, on both the first portion 39 and the second portion 40, and at least one protrusion 72 located on the inner bore 58 of the cap 24, on the second end 28 of the cap 24. The indentation 70 located on the second portion 40 may include a passage 71 and a groove 73.

When the device 10 is in a disengaged position, the at least one indentation 70 and the at least one protrusion 72 are not aligned and the plunger 38 is prevented from downward movement. Thus, the actuating mechanism acts as a safety from accidentally pushing down on the plunger 38 and piercing the stopper 18. An upper end 75 of the at least one protrusion 72 may be rounded so that the upper end 75 of the at least one protrusion 72 rests in the groove 73 when the device 10 is in the disengaged position.

Figure 5A:
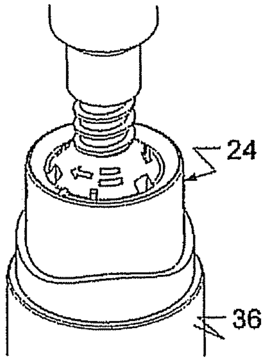
FIGS. 5A-5C are perspective views of the actuation of the reconstitution device of FIG. 1.
Figure 5B:
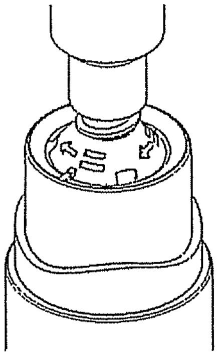
Figure 6:
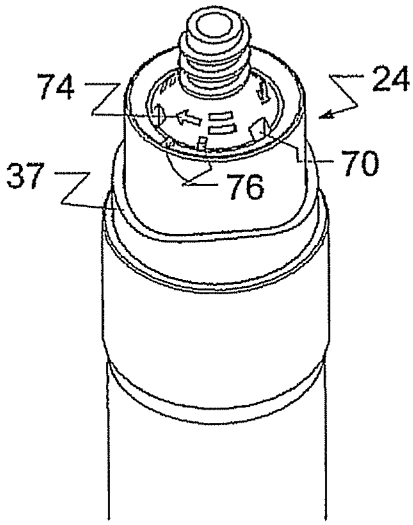
FIG. 6 is a perspective view of a portion of the reconstitution device of FIG. 1.

In order to use the device 10, a user may rotate the plunger 38 a given number of degrees until the at least one indentation 70 aligns with the at least one protrusion 72, as shown in FIGS. 5A and 58. The top surface 41 of the plunger 38 may include direction markers 7 4 to indicate to a user which direction to turn the plunger, as best seen in FIG. 6. The top surface 41 may further include alignment markers 76 to indicate to the user when the actuating mechanism is aligned.

As the user rotates the plunger 38, the at least one protrusion 72 also moves downward so that the at least one protrusion 72 can move from the groove 73 to the passage 71 and then move from the passage 71 to the at least one indentation 70. The movement from the passage 71 to the at least one indentation 70 can provide tactile feedback and/or audible feedback to the user so that the user knows when the plunger 38 has been rotated the given number of degrees and it is acceptable to push the plunger 38 in a downward direction.

The given number of degrees the plunger 38 is rotated to align the at least one indentation 70 with the at least one protrusion 72 depends on various factors. For example, the factors may include: (i) the number of indentations of the at least one indentation 70 and the number of protrusions of the at least one protrusion 72, (ii) the spacing between each protrusion (if more than one protrusion is used), and the spacing between each indentation (if more than one indentation is used), (iii) the position of the at least one indentation 70 relative to the position of the at least one protrusion 72 at the time the device 10 is assembled and/or at the time the plunger 38 is to be rotated, and (iv) the size of the at least one indentation 70 and the size of the at least one protrusion 72 (e.g., each protrusion and indentation may be $\frac{1}{36}^{th}$ (i.e., 10 degrees) of the circumference of the inner bore 58 of the cap 24 and the outer circumference of the plunger 38, respectively).

In one exemplary embodiment, the at least one protrusion 72 includes three protrusions substantially equally spaced around the inner bore 58 of the cap (e.g., substantially spaced one hundred twenty degrees apart), and the at least one indentation 70 includes three indentations substantially equally spaced around the outer circumference of the plunger 38 (e.g., substantially spaced one hundred twenty degrees apart). In accordance with this exemplary embodiment, the given number of degrees the plunger 38 is rotated to align the at least one indentation 70 with the at least one protrusion 72 is preferably is about thirty (30) degrees. However, depending on one or more of the factors described above, the given number of degrees may be substantially between five (5) degrees and one hundred twenty (120) degrees.

Figure 5C:
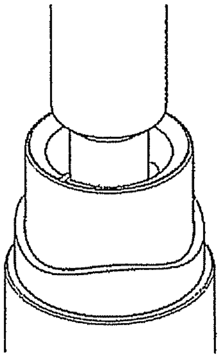

Referring to FIG. 5C, the plunger 38 may then be pushed downwardly into the engaged position so the shaft 42 may pass through the aperture 62 in the cap 24 and pierce the stopper 18. Once the shaft 42 has pierced the stopper 18, the locking mechanism 64 prevents the plunger 38 from being pulled back upwardly to the disengaged position.

The device 10 may include a feedback mechanism that provides a user of the device 10 with feedback regarding operation of the device 10. For example, the feedback may indicate that the shaft 42 has traveled an optimum distance into the stopper 18. Alternatively, or in combination, the feedback may indicate that the plunger 38 has traveled an optimum distance within the cap 24 and that the user should not push the plunger 38 any further. Other examples of the feedback provided by the feedback mechanism are also possible.

The feedback mechanism may be arranged in various configurations. For example, as shown in FIGS. 2 and 3, the feedback mechanism may comprise (i) a convex bump 55 located on the surface of the second portion 40 of the plunger 38 and extending into the indentation 70, and (ii) a convex bump 57 on the protrusion 72.

The convex bump 55 may be molded as part of the second portion 40. The convex bump 55 may extend 0.2 mm to 1.0 mm (preferably 0.3 mm to 0.6 mm) away from the second portion 40. A widest portion of the convex bump 55 may have a diameter between 0.2 mm to 1.0 mm (preferably 0.3 mm to 0.6 mm). The convex bump 57 may be molded as part of the indentation 70. The convex bump 57 may extend 0.2 mm to 1.0 mm (preferably 0.3 mm to 0.6 mm) away from the indentation 70. A widest portion of the convex bump 57 may have a diameter between 0.2 mm to 1.0 mm (preferably 0.3 mm to 0.6 mm).

In operation, and by way of example, as the plunger 38 travels in a direction towards the stopper 18, the feedback mechanism provides tactile feedback as the convex bump 55 on the indentation 70 travels past the convex bump 5 7 on the protrusion 72. The tactile feedback may be felt by the user. Moreover, as the convex bump 55 on the indentation 70 travels past the convex bump 57 on the protrusion 72, a sound may be made such that the feedback mechanism also provides audible feedback.

Figure 7:
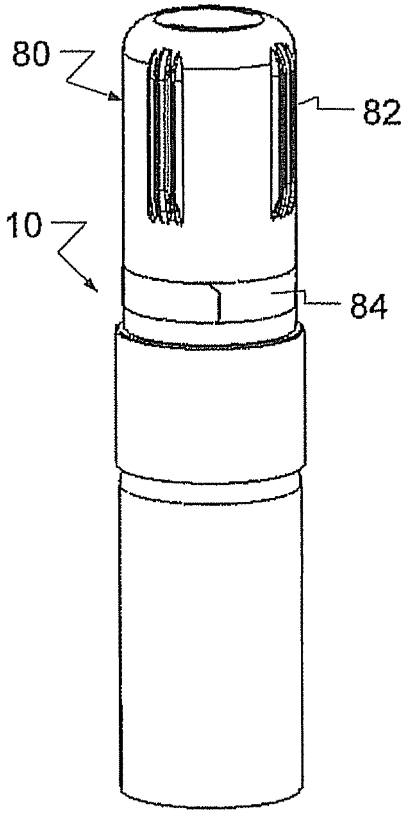
FIG. 7 is a perspective view of the reconstitution device of FIG. 1 including a top.

With reference to FIG. 7, the device 10 may include a top 80 which is positioned over the second end 28 of the cap 24 and the plunger 38. The top 80 protects the plunger 38. The top 80 may further include a textured surface 82 for facilitating gripping and removal of the top 80 by a user. Additionally, a tamper-proof mechanism 84 may be located on the device 10 to indicate to a user whether the device 10 has been used. The tamper-proof mechanism 84 may comprise any type of indicator, such as a seal, a holographic label, or a tab, for example. In operation, the device 10 is in the disengaged position, that is, when the protrusions 72 of the cap 24 and the indentations 70 of the plunger 38 are not aligned, and the shaft 42 of the plunger 38 is not piercing the stopper 18, as shown in FIG. 8A. Once the top 80 is removed from the device 10 by a user, the tamperproof mechanism 84 will be broken. A user may then attach a second receptacle 90, such as a syringe, to the receptacle 12. To activate the device 10, a user may then rotate the plunger 38 about the given number of degrees (e.g., 30 degrees) so the indentations 70 on the plunger 38 align with the protrusions 72 on the cap 24. The plunger 38 may then be pushed in a downward direction toward the stopper 18 into the engaged position, as shown in FIG. 88. The shaft 42 of the plunger 38 may pierce the stopper 18, allowing access to the opening 16 of the receptacle 12. The contents of the second receptacle 90 may then be introduced into the receptacle 12 to mix with the component. The mixed contents may then be pulled back into the second receptacle 90. A needle (not shown) may then be secured to the second receptacle 90, and the complete and active drug may be administered to a patient.

Referring to FIG. 9, a second embodiment 110 of the reconstitution device of the present invention is shown. The device 110 may include a receptacle 112 for storing a first component of a pharmaceutical preparation (not shown), such as its active ingredient, for example. The receptacle 112 may include an opening 116 surrounded or partially surrounded by a neck 114. The neck 114 may also include a lip 115. The opening 116 in the neck 114 allows for a second component, such as a liquid (not shown), to be introduced into the receptacle 112 and mix with the first component. A stopper 118 may be positioned in the opening 116 of the neck 114 to block access to the receptacle 112. The stopper 118 may be made of a relatively non-rigid material, such as elastomer. The stopper 118 may include a top portion 120 located against the lip 115, and a bottom portion 122 located within the opening 116 of the neck 114. The top portion 120 may be capable of being perforated, to allow access to the receptacle 112.

The device 110 may further include a cap 124 secured to the neck 114 of the receptacle 112. The cap 124 may have a first end 126, which is secured to the neck 114 of the receptacle 112, and a second end 128 located opposite the first end 126. The first end 126 of the cap 124 may surround at least a portion of the stopper 118. The first end 126 of the cap 124 may include a protrusion 130 for securing the first end 126 to the lip 115 of the receptacle 112.

The first end 126 of the cap 124 may further be secured to the receptacle 112 by a crimp ring 132, which may be positioned in an indentation 125 in the first end 126 of the cap 124. The crimp ring 132 may extend completely or around only a portion of the circumference of the first end 126 of the cap 124. The crimp ring 132 may be made of metal or a polymer with low creep sensitivity. The crimp ring 132 may further include an upper surface 134 for attaching to a top 180, which will be described below.

The device 110 may include a plunger 138 located at the second end 128 of the cap 124. The plunger 138 may include a shaft 142 extending in a direction towards the stopper 118. The shaft 142 may include a pointed end 144 for piercing the top portion 120 of the stopper 118, thereby allowing the shaft 142 access to the receptacle 112. The shaft 142 may further include a filtering mechanism (not shown) similar in structure and function to the filtering mechanism disclosed above with respect to device 10.

The plunger 138 may also include a male element 148 extending in a direction opposite the shaft 142. The male element 148 may be configured to receive a second receptacle (not shown), such as a syringe, for example. The male element 148 may include an inner bore 150 and an outer surface 151. The outer surface 151 may include a thread 152 for mating with the second receptacle.

The shaft 142 of the plunger 138 may also include first and second longitudinal channels (not shown) which establish communication between the receptacle 112 and the inner bore 150 of the male element 148. The longitudinal channels are similar in structure and function to the longitudinal channels described above with respect to device 10. The plunger 138 may further be configured to slide along the outer circumference of the cap 124, as shown in FIG. 9.

The cap 124 may further include an inner bore 158 having an annular plate 160 with an aperture 162. The aperture 162 is coaxially aligned with the shaft 142 of the plunger 138. When the plunger 138 moves downward toward the receptacle 112, the shaft 142 moves downwardly through the aperture 162 to pierce the top portion 120 of the stopper 118.

The device 110 may include a mechanism that prevents upward movement of the plunger 138 after downward movement of the plunger 138 towards the stopper 118 has occurred. As an example, the device 110 may include a locking mechanism such as the locking mechanism 64 described above. The locking mechanism may be used to retain the plunger 138 to the device 110.

As another example, the device 110 may include a ratcheting mechanism that prevents upward movement of the plunger 138 after downward movement of the plunger 138 towards the stopper 118 has occurred. The ratcheting mechanism may be used to retain the plunger to the device 110.

Figure 10:
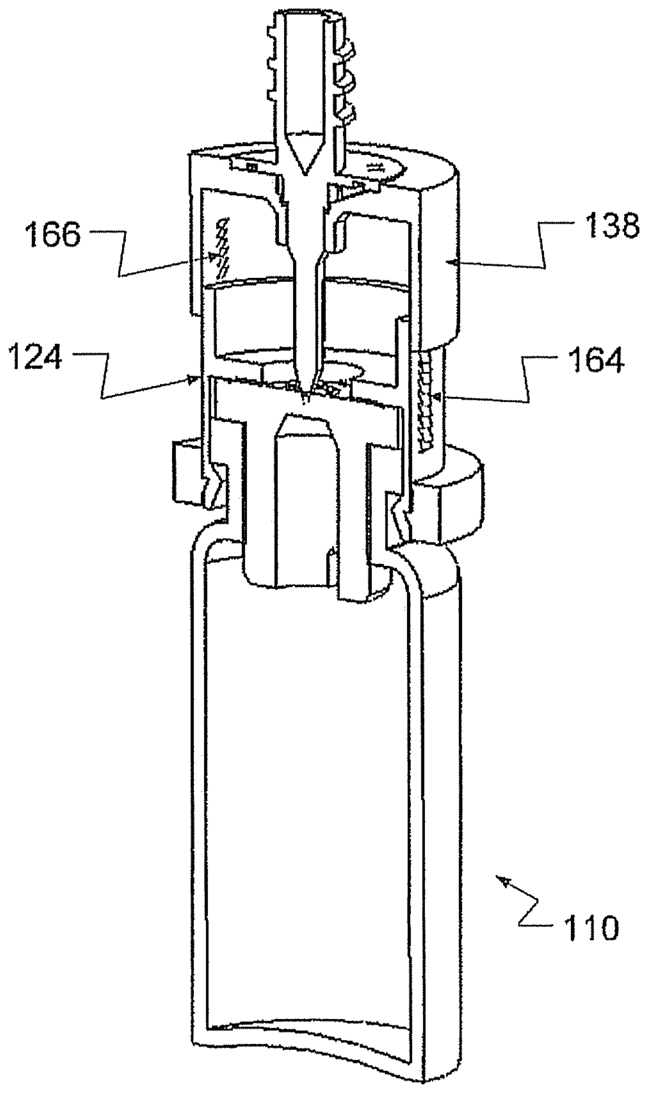
FIG. 10 is a cross-sectional view of the reconstitution device of FIG. 9 including a ratcheting mechanism.

The ratcheting mechanism may include one or more series of ribs and one or more series of teeth. Each of the one or more series of ribs corresponds to one of the series of teeth. FIG. 10 shows the device 110 including (i) a series of ribs 164 located on an outer surface of the cap 124, and (ii) a series of teeth 166 located on an inner surface of the plunger 138. The series of ribs 164 corresponds to another set of teeth (not shown) located on the inner surface of the plunger 138. The series of teeth 166 corresponds to another series of ribs (not shown) located on the outer surface of the cap 124.

In this way, as the plunger 138 is moved in a downward direction towards the stopper 118, one or more teeth of a series of teeth (not shown) travel over the series of ribs 164, whereas if upward movement of the plunger 138 is attempted, one or more teeth of the series of teeth (not shown) encounter the series of ribs 164 so as to prevent the one or more teeth as well as the plunger 138 from moving upwards. Similarly, as the plunger 138 is moved in a downward direction towards the stopper 118, one or more teeth of a series of teeth 166 travel over a series of ribs (not shown), whereas if upward movement of the plunger 138 is attempted, one or more teeth of the series of teeth 166 encounter the series of ribs (not shown) so as to prevent the series of teeth 166 as well as the plunger 138 from moving upwards.

The cap 124 and plunger 138 of the device 110 may further include an actuating mechanism similar in structure and function to the actuating mechanism described above with respect to the device 10.

Figure 11:
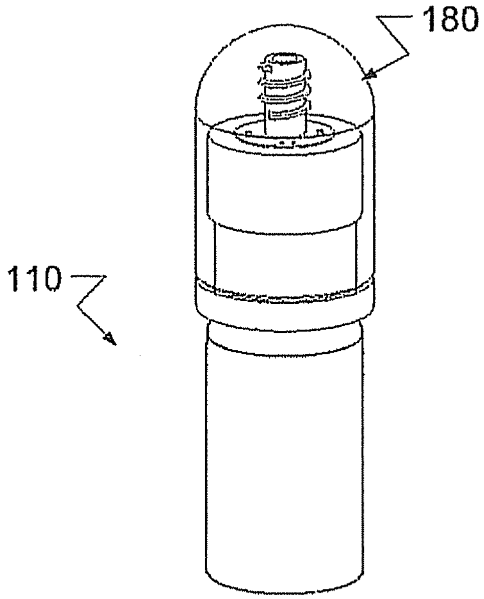
FIG. 11 is a perspective view of the reconstitution device of FIG. 9 including a top.

The device 110 may include a top 180, as shown in FIG. 11, which fits over the second end 128 of the cap 124 and the plunger 138, and attaches to the crimp ring 132. The top 180 protects the device 110.

Moreover, the top 180 and the crimp ring 132 may be formed as a single piece (i.e., a top and crimp ring combination (not shown)). To accommodate the top and crimp ring combination, the cap 124 may have a first end and a second end, and the first end may be larger in diameter than the second end (similar to the first end 26 of the cap 24 and the second end 28 of the cap 24 shown in FIG. 1). In this way, the top and crimp ring combination may slide over the plunger 138 so as to allow the cap 124 to be secured to the receptacle 112. To use the device 110 with the top and crimp ring combination, the top may be broken off (e.g., by twisting the top) and the crimp ring continues to secure the cap 124 to the receptacle 112.

Additionally, a tamper-proof mechanism (not shown) may be located on the device 110 to indicate to a user whether the device has been used. The tamperproof mechanism may comprise any type of indicator, such as a seal, a holographic label, or a tab, for example.

In operation, the device 110 is in a disengaged position, that is, the shaft 142 of the plunger 138 is not piercing the stopper. Once the top 180 is removed from the device 110, the tamper-proof mechanism will be broken. A user may then attach a second receptacle, such as a syringe, to the receptacle 112. The plunger 138 may then be pushed in a downward direction toward the stopper 118 into an engaged position. The shaft 142 of the plunger 138 may pierce the stopper 118, allowing access to the opening 116 of the receptacle 112. The contents of the second receptacle may then be introduced into the receptacle 112 to mix with the component. The mixed contents may then be pulled back into the second receptacle. A needle (not shown) may then be secured to the second receptacle, and the complete and active drug may be administered to a patient.

While certain features and embodiments of the present invention have been described in detail herein, it is to be understood that the invention encompasses all modifications and enhancements within the scope and spirit of the following claims.

What is claimed is:

1. A reconstitution device, comprising:

a receptacle;

a cap including a first end, a second end, and an inner bore having a central aperture, the first end being secured to the receptacle;

a stopper located between the receptacle and the cap, the stopper including a portion capable of being perforated;

a plunger secured to the second end of the cap, the plunger comprising a shaft for perforating the stopper;

a locking mechanism located in the cap comprising a thin material including a tongue capable of flexing in a vertical direction; and an actuating mechanism, characterized in that the locking mechanism further comprises a tab that connects to the tongue, wherein the tongue is located within an aperture within the locking mechanism, and wherein the tongue comprises an aperture that is coaxially aligned with the shaft of the plunger.

2. The device of claim 1, wherein the actuating mechanism comprises at least one protrusion on the cap and at least one indentation on the plunger, wherein the plunger is rotatable for aligning the at least one protrusion with the at least one indentation, and wherein the plunger is movable in a downward direction when the at least one protrusion is aligned with the at least one indentation.

3. The device of claim 2, further comprising:

a feedback mechanism for indicating to a user when the plunger has pierced the stopper.

4. The device of claim 3, wherein the feedback mechanism comprises a convex bump on each of the at least one protrusion on the cap, and a convex bump on each of the at least one indentation on the plunger.

5. The device of claim 2, further comprising:

a feedback mechanism for indicating to a user when the plunger has rotated such that the at least one protrusion aligns with the at least one indentation.

6. The device of claim 5, wherein the feedback mechanism provides tactile feedback and audible feedback.

7. The device of claim 1, wherein the receptacle includes an opening surrounded by a neck for attaching to the first end of the cap, the stopper being located in the opening of the neck.

8. The device of claim 7, wherein the first end of the cap is secured to the neck of the receptacle by a crimp ring.

9. The device of claim 7, wherein the first end of the cap is secured to the receptacle by a C-clip.

10. The device of claim 1, wherein the plunger further includes a male element for receiving a second receptacle, wherein the second receptacle is a syringe, and wherein the male element includes an inner bore and an outer surface including a thread.

11. The device of claim 1, wherein the plunger is adapted to slide along the inner bore of the cap.

12. The device of claim 1, wherein, when the plunger is pulled upwardly, the shaft pulls upwardly on the tongue to cause the tongue to flex vertically in an upward direction, and wherein the flexing of the tongue causes the aperture to change from a first shape when the aperture is perpendicular to the shaft to a second shape when the aperture is not perpendicular to the shaft.

13. The device of one of claims 1 to 12, wherein the plunger has a top surface including direction markers and alignment markers.

* * * * *